US 10,147,171 B2

(12) United States Patent
Brown et al.

(10) Patent No.: US 10,147,171 B2
(45) Date of Patent: Dec. 4, 2018

(54) SYSTEMS AND METHODS FOR GENERATING SUBTRACTED IMAGES

(71) Applicant: General Electric Company, Schenectady, NY (US)

(72) Inventors: Todd Brown, Tooele, UT (US); Timothy Skuster, Salt Lake City, UT (US); James Zhengshe Liu, Salt Lake City, UT (US)

(73) Assignee: General Electric Company, Schenectady, NY (US)

(*) Notice: Subject to any disclaimer, the term of this patent is extended or adjusted under 35 U.S.C. 154(b) by 91 days.

(21) Appl. No.: 15/272,270

(22) Filed: Sep. 21, 2016

(65) Prior Publication Data

US 2018/0082420 A1   Mar. 22, 2018

(51) Int. Cl.
  *A61B 6/00*      (2006.01)
  *G06T 5/50*      (2006.01)
  *G06T 11/00*     (2006.01)
  *G06T 7/00*      (2017.01)

(52) U.S. Cl.
  CPC ............... *G06T 5/50* (2013.01); *A61B 6/469* (2013.01); *A61B 6/481* (2013.01); *A61B 6/487* (2013.01); *A61B 6/5205* (2013.01); *G06T 11/008* (2013.01); *G06T 7/0016* (2013.01); *G06T 2200/24* (2013.01); *G06T 2207/10016* (2013.01); *G06T 2207/10121* (2013.01); *G06T 2207/20104* (2013.01); *G06T 2207/20224* (2013.01); *G06T 2207/30004* (2013.01); *G06T 2207/30101* (2013.01)

(58) Field of Classification Search
None
See application file for complete search history.

(56) References Cited

U.S. PATENT DOCUMENTS

| 5,031,620 A * | 7/1991 | Oe | H04N 5/3205 |
|---|---|---|---|
| | | | 348/E5.089 |
| 7,725,165 B2 | 5/2010 | Chen et al. | |
| 8,111,895 B2 | 2/2012 | Spahn | |
| 8,218,727 B2 | 7/2012 | Baumgart et al. | |
| 8,509,384 B2 | 8/2013 | Spahn | |
| 8,553,963 B2 | 10/2013 | Rauch et al. | |

(Continued)

OTHER PUBLICATIONS

Extended European Search Report and Opinion issued in connection with corresponding EP Application No. 17191274.4 dated Nov. 17, 2017.

*Primary Examiner* — Justin P. Misleh
(74) *Attorney, Agent, or Firm* — McCoy Russell LLP

(57) ABSTRACT

Methods and systems are provided for generating regional digital subtraction angiography (DSA) images and roadmap images with landmarks. In one embodiment, a method comprises generating a mask from a set of mask images of an anatomy of a subject, and generating a masked image by applying the mask to acquired image data of the anatomy of the subject, including weighting the mask differently inside a region of interest (ROI) of the image than outside the ROI, the weighting inside ROI independent of the weighting outside the ROI. In this way, a user may be able to adjust a relative magnitude of subtraction inside and outside the ROI, and thus be able to visualize both vasculature and landmarks within the same image frame.

19 Claims, 7 Drawing Sheets

(56) References Cited

U.S. PATENT DOCUMENTS

| | | | |
|---|---|---|---|
| 2007/0140427 A1* | 6/2007 | Jensen | A61B 6/481 378/98.12 |
| 2007/0195931 A1* | 8/2007 | Ohishi | A61B 6/504 378/98.2 |
| 2008/0051648 A1* | 2/2008 | Suri | A61B 6/481 600/407 |
| 2008/0137935 A1* | 6/2008 | Spahn | G06T 5/50 382/132 |
| 2008/0260092 A1* | 10/2008 | Imai | A61B 6/032 378/5 |
| 2009/0257631 A1* | 10/2009 | Baumgart | G06T 5/50 382/128 |
| 2013/0019193 A1* | 1/2013 | Rhee | G06F 3/0486 715/769 |
| 2014/0133731 A1* | 5/2014 | Baumgart | A61B 6/481 382/132 |
| 2014/0198131 A1 | 7/2014 | Rudin et al. | |
| 2015/0150526 A1 | 6/2015 | Ohishi | |
| 2015/0213600 A1 | 7/2015 | Kyriakou | |
| 2016/0253803 A1* | 9/2016 | Miyamoto | A61B 6/481 382/132 |
| 2017/0116730 A1* | 4/2017 | Yamanaka | G06T 7/0012 |

* cited by examiner

SYSTEMS AND METHODS FOR GENERATING SUBTRACTED IMAGES

FIELD

Embodiments of the subject matter disclosed herein relate to subtraction techniques used in imaging system and more particularly, to digital subtraction angiography (DSA) and roadmapping techniques used in x-ray imaging systems.

BACKGROUND

Angiography is an imaging technique used to visualize the blood vessels or vasculature of an anatomy of a patient by means of x-ray imaging. Typically, a contrast medium is injected into a blood vessel and imaged using x-ray based techniques such as fluoroscopy. Image subtraction techniques are then applied to remove unwanted bony structures from the fluoroscopic image of the anatomy to enhance visibility of the vasculature of the anatomy being examined. Subtracted images may be displayed using one of two imaging modes, namely digital subtraction angiography (DSA) and roadmapping. Briefly, DSA is a mode tailored for viewing the flow of contrast media through the vasculature of the anatomy and roadmapping is tailored for interventional access via vasculature, which have been filled with contrast media or $CO_2$. In both imaging modes, the resulting images generated using such subtraction techniques may enhance visualization aspects of the image but lead to loss of anatomical landmarks. Loss of anatomical landmarks may cause delays in the diagnostics and clinical evaluations performed by the user. Without the anatomical landmarks, it may be difficult to insert and place interventional devices inside the vasculature, leading to errors in the placement of such devices.

BRIEF DESCRIPTION

In one embodiment, a method comprises generating a mask from a set of mask images of an anatomy of a subject, and generating a masked image by applying the mask to acquired image data of the anatomy of the subject, including weighting the mask differently inside a region of interest (ROI) of the image data than outside the ROI, the weighting inside ROI independent of the weighting outside the ROI. The weighting includes subtracting a first amount of the mask from a first region inside the ROI and subtracting a second amount of the mask from a second region outside the ROI. In this way, the masked image may include both the subtracted and unsubtracted image. In addition, each of the first amount and the second amount may be dynamically adjusted by a user. In this way, the user may be able to adjust a relative magnitude of subtraction inside and outside the ROI, and thus be able to visualize both vasculature and landmarks within the same image frame. As a result, the time taken for diagnostic evaluation may be reduced, and an accuracy of diagnostics may be increased.

It should be understood that the brief description above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

The present invention will be better understood from reading the following description of non-limiting embodiments, with reference to the attached drawings, wherein below.

DETAILED DESCRIPTION

Figure 3A:
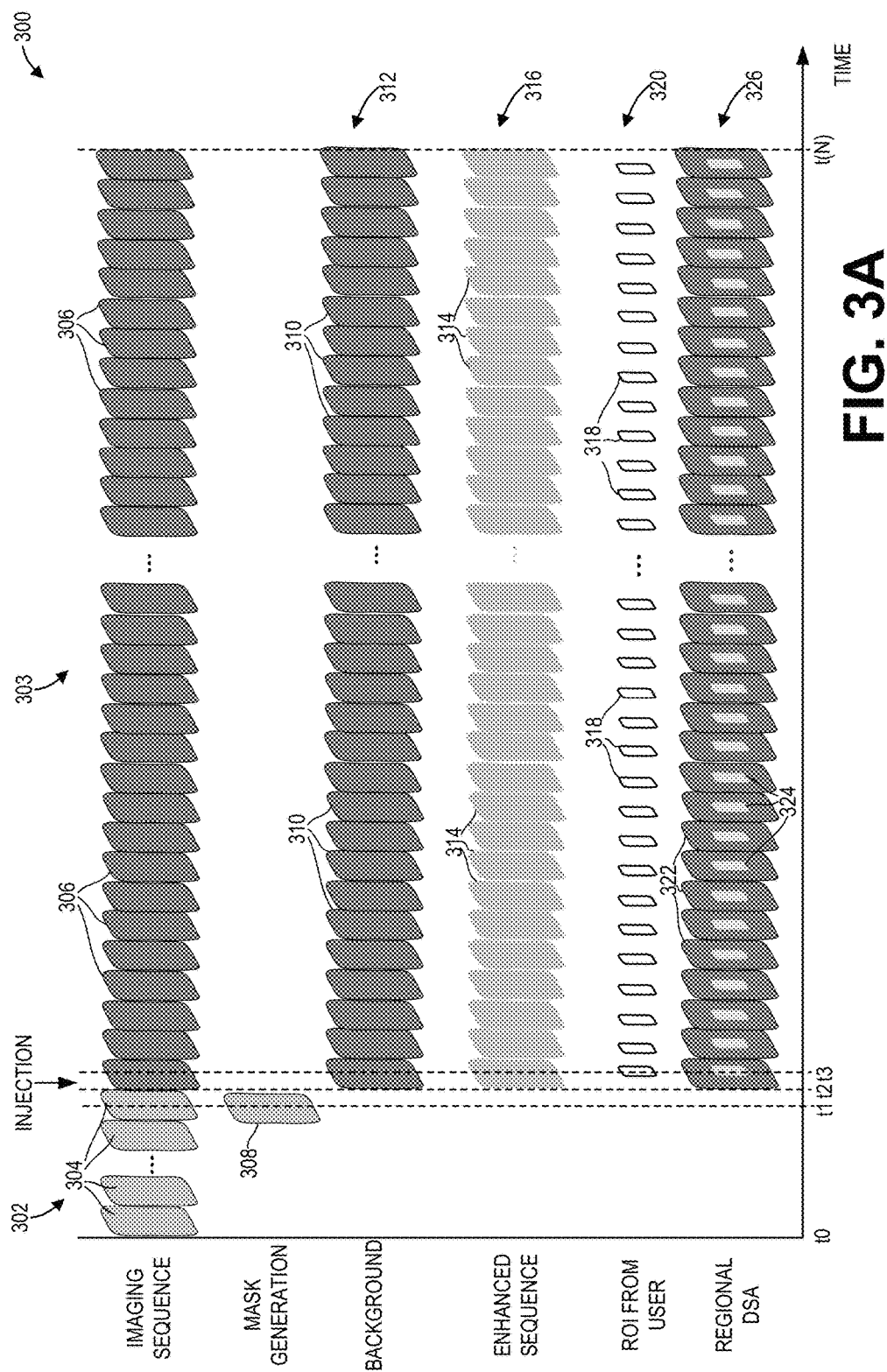
FIG. 3A is an example regional digital subtraction angiography (DSA) sequence having different levels of a DSA mask subtracted from inside and outside a region of interest (ROI) according to an embodiment of the invention.
Figure 3B:
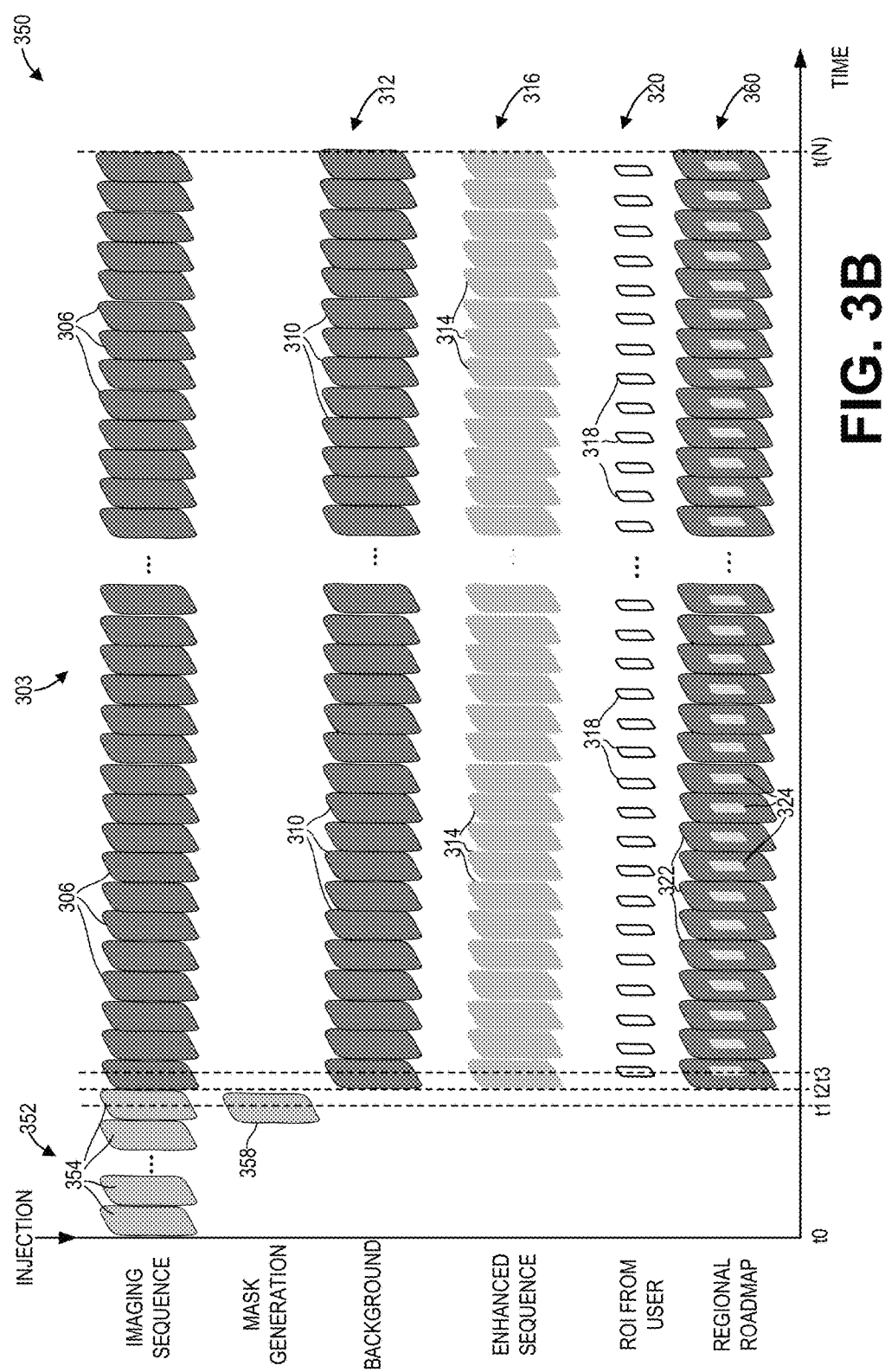
FIG. 3B is an example regional roadmap sequence having different levels of a roadmap mask subtracted from inside and outside the ROI according to an embodiment of the invention.
Figure 4:
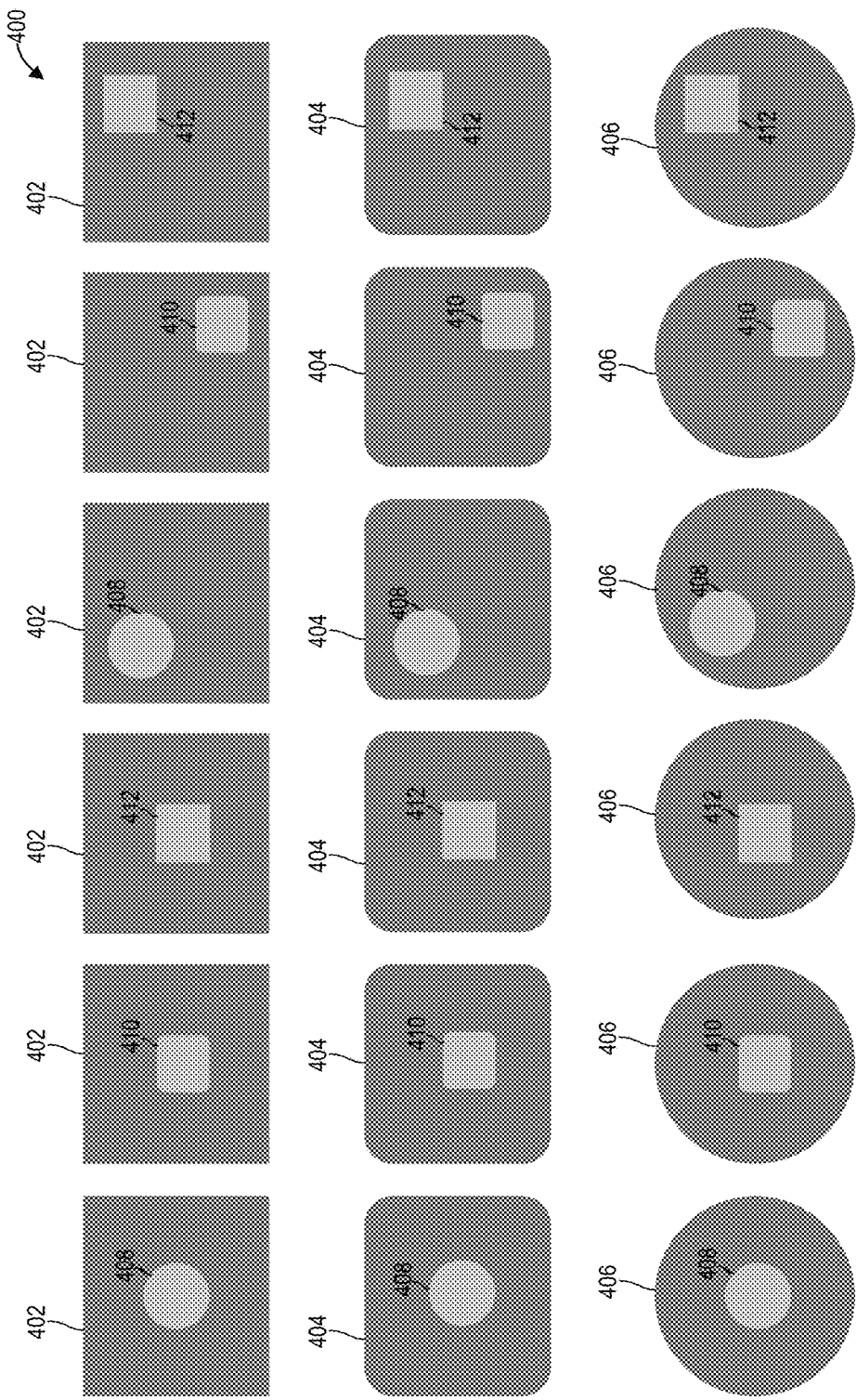
FIG. 4 shows some example shapes and locations of the ROI according to an embodiment of the invention.
Figure 5:
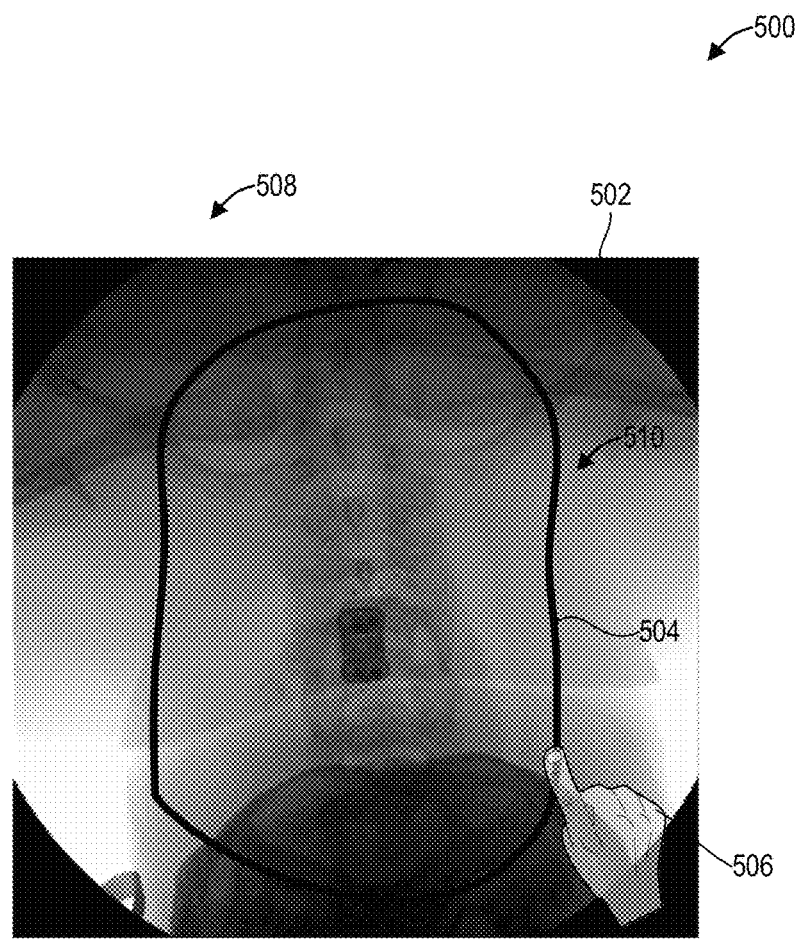
FIG. 5 shows an anatomy of a subject with a user-defined ROI according to an embodiment of the invention.

The following description relates to various embodiments for subtraction techniques used in imaging systems. In particular, systems and methods are provided for applying digital subtraction angiography (DSA) and roadmapping techniques in imaging systems depicted in FIGS. 1 and 2. A mask is generated from a series of mask frames acquired at the beginning of an imaging sequence as shown in FIGS. 3A-B. Specifically, in DSA imaging, a DSA mask is generated from a set of mask frames acquired before injecting a contrast agent into an anatomy of a subject (FIG. 3A), and in the roadmapping technique, a roadmap mask is generated by applying a peak opacification function to a series of mask frames acquired after the injection of the contrast agent (FIG. 3B). A masked image may be generated by applying the mask to acquired image data of the anatomy, including weighting the mask differently inside a region of interest (ROI) of the image than outside the ROI. The ROI may be selected by a user from a set of pre-defined set of shapes as shown in FIG. 4. In one example, the user may draw the ROI based on a size and shape of the anatomy as shown in FIG. 5. The user may also dynamically adjust a size, a shape, and a location of the ROI in real-time by performing operations as shown in FIGS. 6A-D. A method for generating the masked image by subtracting different amounts of the mask from the region inside the ROI than outside is shown in FIG. 7. In this way, the user may be able to adjust a level of subtraction applied to different regions of the masked image and generate regionally subtracted images.

Though the subtraction techniques used in imaging systems are described herein with regard to an x-ray system by way of example, it should be understood that the present techniques may also be useful when applied to images acquired using other imaging modalities, such as tomosynthesis, MRI, C-arm angiography, and so forth. The present discussion of an x-ray imaging modality is provided merely as an example of one suitable imaging modality.

Further, as used herein, the term "image" broadly refers to both viewable images and data representing a viewable image. However, many embodiments generate (or are configured to generate) at least one viewable image.

Figure 1:
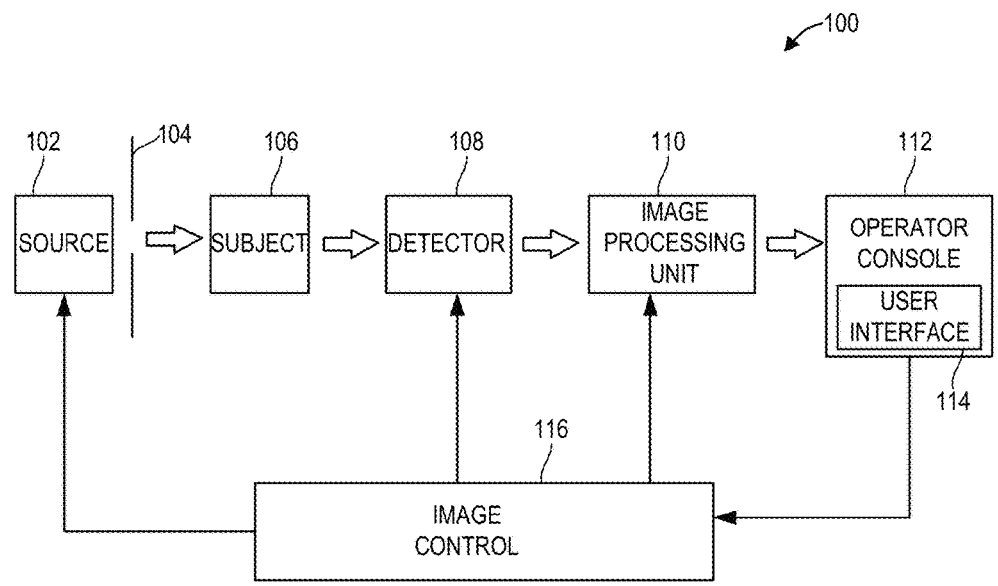
FIG. 1 is a block diagram of an imaging system, according to an embodiment of the invention.

Turning now to FIG. 1, a block diagram of an example imaging system 100 is shown. The imaging system 100 may be configured to allow fast and iterative image generation. Particularly, the imaging system 100 may configured to image a subject 106 such as a patient, an inanimate object, one or more manufactured parts, and/or foreign objects such as dental implants, stents, and/or contrast agents present within the body. In one embodiment, the imaging system 100 may include a gantry, which in turn, may further include at least one x-ray radiation source 102 configured to project a beam of x-ray radiation for use in imaging the patient. Specifically, the radiation source 102 is configured to project the x-rays through a collimator 104 towards a detector 108 positioned on the opposite side of the gantry (explained with reference to FIG. 2). Although FIG. 1 depicts only a single radiation source 102, in certain embodiments, multiple radiation sources may be employed to project a plurality of x-rays for acquiring projection data corresponding to the patient at different energy levels to increase the scanned volume size, or to scan a volume more quickly. In one non-limiting example, the source 102 may be a source producing x-rays having a spectrum of energies that range, typically, from 30 keV to 120 keV. The radiation from the source 102 may pass through the subject 106 and, after being attenuated, impinge upon the detector or detector assembly 108. The detector 108 may produce an analog electrical signal that represents the intensity of an impinging radiation beam, and hence the attenuated beam, as it passes through the subject 106. In one example, the detector 108 may be a direct-conversion type detector (e.g., amorphous selenium detector, CZT detectors, etc.). Other examples of the detector 108 include Cesium Iodide (CsI) and complementary metal-oxide-semiconductor (CMOS) detectors. In one example, the imaging system 100 may a mobile surgical system or an interventional system (cath lab).

In certain embodiments, the imaging system 100 further includes an image processing unit 110 configured to generate fluoroscopic images of a target volume of the patient using an iterative or analytic image generation methods as explained with reference to FIGS. 3A-B.

An image control system 116 may communicate with the image processing unit 110 to enable an operator, using an operator console 112, to control the scanning parameters and to view the generated image on a display (not shown in FIG. 1). Operator console 112 may include some form of operator or user interface 114, such as a keyboard, mouse, voice activated controller, or any other suitable input apparatus that allows the operator to control the image control system 116 and view the generated fluoroscopic image or other data from the image processing unit 110 on the display as explained in detail with reference to FIG. 2. In some example, the user may select a ROI within the image by performing operations using the user interface 114. Additionally, the operator console 112 may allow the operator to store the generated image in a storage device, which may include hard drives, floppy discs, compact discs, etc. The operator may also use the console 112 to provide commands and instructions to the image control system 116 for controlling the source 102 that provides power and timing signals to the source 102, and additionally for controlling the detector 108, including adjusting gain and filtering capabilities of the detector.

Figure 2:
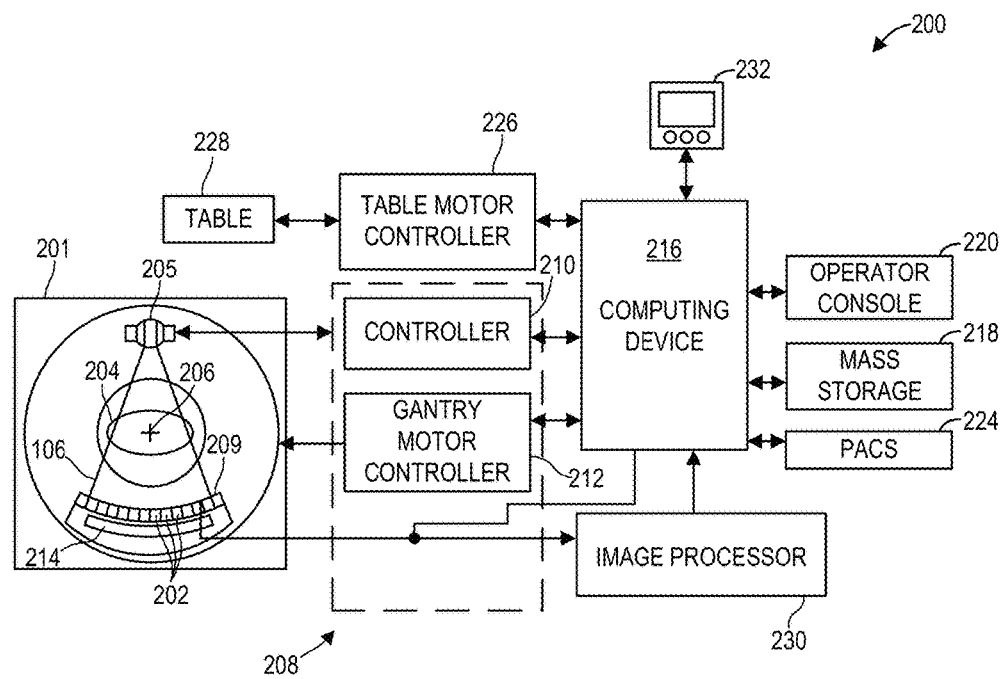
FIG. 2 is a schematic diagram of the imaging system including a user display for displaying acquired fluoroscopic images according to an embodiment of the invention.

FIG. 2 illustrates an exemplary imaging system 200 similar to the imaging system 100 of FIG. 1. In accordance with aspects of the present disclosure, the system 200 is configured to generate fluoroscopic images with a user-specified temporal window in real-time. Herein, the imaging system may be a real-time system that receives image data, processes the image data, and displays the image data within a specified period, without any post-processing delays. In one embodiment, the system 200 includes a source 205 and a detector 209. The source 205 may be a non-limiting example of the source 102 of FIG. 1, and the detector 209 may be a non-limiting example of the detector 108 shown in FIG. 1. The detector 209 further includes a plurality of detector elements 202 that together sense the radiation (e.g., x-ray beams) that pass through a subject 204 to generate a corresponding fluoroscopic image. Accordingly, in one embodiment, the detector 209 is fabricated in a multi-slice configuration including the plurality of rows of cells or detector elements 202.

In certain embodiments, the system 200 is configured to traverse different angular positions around the subject 204 for acquiring desired projection data. Accordingly, a gantry 201 and the components mounted thereon may be configured to rotate about a center of rotation 206 for acquiring image data, for example, at different energy levels. Alternatively, the mounted components may be configured to move along a general curve rather than along an arc of a circle.

In one embodiment, the system 200 includes a control mechanism 208 to control movement of the components such as rotation of the gantry 201 and the operation of the source 205. In certain embodiments, the control mechanism 208 further includes a controller 210 configured to provide power and timing signals to the radiation source 205. The controller 210 may be a non-limiting example of the image control system 116 shown in FIG. 1. Additionally, the control mechanism 208 includes a gantry motor controller 212 configured to control a rotational speed and/or position of the gantry 201 based on imaging requirements.

In certain embodiments, the control mechanism 208 further includes a data acquisition system (DAS) 214 configured to sample analog data received from the detector elements 202 and convert the analog data to digital signals for subsequent processing. The data sampled and digitized by the DAS 214 is transmitted to a computing device 216. In one example, the computing device 216 stores the data in a storage device 218. The storage device 218, for example, may include a hard disk drive, a floppy disk drive, a compact disk-read/write (CD-R/W) drive, a Digital Versatile Disc (DVD) drive, a flash drive, and/or a solid-state storage device.

Additionally, the computing device 216 provides commands and parameters to one or more of the DAS 214, the x-ray controller 210, and the gantry motor controller 212 for controlling system operations such as data acquisition and/or processing. In certain embodiments, the computing device 216 controls system operations based on operator input. The computing device 216 receives the operator input, for example, including commands and/or scanning parameters and/or region of interest (ROI) via an operator console 220 operatively coupled to the computing device 216. The operator console 220 may include a keyboard (not shown) or a touchscreen to allow the operator to specify the commands, ROI, and/or scanning parameters. The operator console 220 may be a non-limiting example of the operator console 112 shown in FIG. 1.

Although FIG. 2 illustrates only one operator console 220, more than one operator console may be coupled to the system 200, for example, for inputting or outputting system parameters, requesting examinations, and/or viewing images. Further, in certain embodiments, the system 200 may be coupled to multiple displays, printers, workstations, and/or similar devices located either locally or remotely, for example, within an institution or hospital, or in an entirely different location via one or more configurable wired and/or wireless networks such as the Internet and/or virtual private networks.

In one embodiment, for example, the system 200 either includes, or is coupled to a picture archiving and communications system (PACS) 224. In an exemplary implementation, the PACS 224 is further coupled to a remote system such as a radiology department information system, hospital information system, and/or to an internal or external network (not shown) to allow operators at different locations to supply commands and parameters and/or gain access to the image data.

The computing device 216 uses the operator-supplied and/or system-defined commands and parameters to operate a table motor controller 226, which in turn, may control a motorized table 228. Particularly, the table motor controller 226 moves the table 228 to appropriately position the subject 204 in the gantry 201 for acquiring projection data corresponding to the target volume of the subject 204.

As previously noted the DAS 214 samples and digitizes the projection data acquired by the detector elements 202. Subsequently, an image processor 230 uses the sampled and digitized x-ray data to perform high-speed image subtraction, reconstruction, and the like. The image processor 230 may be a non-limiting example of the image processing unit 110 shown in FIG. 1. Although FIG. 2 illustrates the image processor 230 as a separate entity, in certain embodiments, the image processor 230 may form part of the computing device 216. Alternatively, the image processor 230 may be absent from the system 200 and instead the computing device 216 may perform one or more functions of the image processor 230. Moreover, the image processor 230 may be located locally or remotely, and may be operatively connected to the system 200 using a wired or wireless network. Particularly, one exemplary embodiment may use computing resources in a "cloud" network cluster for the image processor 230.

In one embodiment, the image processor 230 reconstructs the images stored in the storage device 218. Alternatively, the image processor 230 transmits the images to the computing device 216 for generating useful patient information for diagnosis and evaluation. In certain embodiments, the computing device 216 transmits the reconstructed images and/or the patient information to a display 232 communicatively coupled to the computing device 216 and/or the image processor 230.

The various methods and processes described further herein may be stored as executable instructions in non-transitory memory on a computing device in system 200. In one embodiment, image processor 230 may include such instructions in non-transitory memory, and may apply the methods described herein to reconstruct an image from scanning data. In another embodiment, computing device 216 may include the instructions in non-transitory memory, and may apply the methods described herein, at least in part, to an image data after receiving the image data from image processor 230. In yet another embodiment, the methods and processes described herein may be distributed across image processor 230 and computing device 216.

In one embodiment, the display 232 allows the operator to evaluate the imaged anatomy. The display 232 may also allow the operator to select a region of interest (ROI) and/or request patient information, for example, via a graphical user interface (GUI) for a subsequent scan or processing. The ROI may include various shapes including, but not limited to, a circle, a squircle, a square, and an ellipse, as shown in FIG. 4. The ROI may also include a user-specified shape based on an anatomy of interest, as shown in FIG. 5.

In some example embodiments, the image processor 230 and/or the computing device 216 may generate a mask from a set of mask images as explained with reference to FIGS. 3A-B, and subsequently apply the mask differently inside a ROI selected by a user (via the operating console 220, for example) than outside the ROI, to generate a regionally subtracted image having landmarks on the outside, to aid the user in diagnosing vascular diseases and/or placing catheters, wires, stents, and the like.

Various embodiments may be implemented in connection with different types of imaging systems. For example, various embodiments may be implemented in connection with an imaging system in which an x-ray source projects a fan- or cone-shaped beam that is collimated to lie within an x-y plane of a Cartesian coordinate system and generally referred to as an "imaging plane." The x-ray beam passes through an object being imaged, such as a patient. The beam, after being attenuated by the object, impinges upon an array of radiation detectors. The intensity of the attenuated radiation beam received at the detector array is dependent upon the attenuation of an x-ray beam by the object. Each detector element of the array produces a separate electrical signal that is a measurement of the beam intensity at the detector location. The intensity measurement from all the detectors is acquired separately to produce a transmission profile.

Turning now to FIGS. 3A-B, imaging sequences generated using DSA and roadmapping methods are shown. Specifically, FIG. 3A illustrates a regional DSA imaging sequence 300. FIG. 3B shows a regional roadmap sequence 350. DSA is an x-ray procedure for observing vasculature of an anatomy of interest by viewing a flow of contrast media through the vasculature. Roadmapping is an x-ray procedure in which a fluoroscopic image is subtracted from densely opacified vessel for enhanced visualization of the vessel and interventional devices.

Typically, a mask is created from a sequence of fluoroscopic images acquired during or after injection of a contrast material into an anatomy of a subject. The mask includes digital information (e.g., pixel output values) of the anatomy including bone structures and vasculature, which is then used as a subtraction template. Once the mask is generated and stored in memory, real-time fluoroscopic images that are captured by the detector of the imaging system are then converted from analog to digital information and subtracted pixel for pixel from the mask. Materials common to both the fluoroscopic image and the mask (e.g., bone and soft tissue) are subtracted, and only the vasculature of the anatomy is displayed.

The process of generating the regional DSA sequence and the regional roadmap sequence may be similar; however, the process of mask generation may be different for the two sequences. FIGS. 3A-B are explained together in the section below while pointing out the differences between the two methods.

At time t0, an anatomy of interest of a subject is positioned in an imaging system and fluoroscopic images of the anatomy of interest are generated as described previously. The imaging system may be a non-limiting example of the imaging system 100 shown in FIG. 1, and/or imaging system 200 shown in FIG. 2. The subject is positioned such that x-rays generated by a source of the imaging system are incident on the anatomy of interest. The tissue and bones of the subject absorb a portion of the incident x-ray radiation. The detector captures the attenuated x-ray radiation, and generates a mask sequence 302. The mask sequence 302 includes a series of mask frames 304. In the regional DSA sequence 300, the mask frames 304 are acquired between time t0 and t1, prior to the injection of a contrast agent, following which a fluoroscopic sequence 303 is acquired. The fluoroscopic image sequence 303 may include several fluoroscopic frames 306. The difference between the mask sequence and the fluoroscopic sequence is that the mask sequence does not include a contrast agent, and hence only has background information of bones and vessels as described later. The fluoroscopic sequence includes frames with the presence of contrast agent, and hence includes details of the flow of the contrast agent though the vasculature.

The number of frames acquired during the mask sequence 302 and/or the fluoroscopic sequence 303 may varied by a user, based on the noise levels in the imaging system, and/or anatomy being imaged, time for which the anatomy is imaged, and the like. In one example, four frames may be acquired during the mask sequence 302 in the interval between time t0 and t1. In another example, eight mask frames may be acquired between time t0 and t1. In yet another example, sixteen mask frames may be acquired between time t0 and t1. Typically, the mask frames 304 are averaged together to generate a mask 308 (interchangeably referred to as a DSA mask). The mask 308 generated by averaging the mask frames 304 may result in the mask 308 having lower noise compared to the noise levels of a single frame 304 as the noise decreases with the inverse square root of the number of frames averaged. Thus, a mask generated by averaging four mask frames may have higher noise than a mask generated by averaging eight mask frames.

Several averaging methods (e.g., integration averaging and recursive averaging) may be used to generate the mask 308. In one example, each individual mask frame may be represented as m(k), and the mask 308 may be represented as M. The mask M may be generated by applying an averaging method described by equation (1A) shown below:

$$\text{Mask, } M = \frac{1}{N} \sum_{k=0}^{N-1} m(k) \tag{1A}$$

where N represents the total number of mask frames that are averaged together to generate the mask M. The mask 308 includes background information of the tissues and the bone structure of the anatomy of interest, and does not include any details of the vasculature as the mask 308 (and the mask frames 304) does not include any contrast material. Said another way, the DSA mask M is generated by averaging pre-contrast mask frames as shown by equation (1A). Once the mask 308 is generated at time t1, a contrast agent or dye (e.g., iodiane contrast agent, gadolinium contrast agent, and the like) may be injected into the anatomy of interest at time t2. Typically, the contrast agent is a clear liquid, which shows dark on x-ray images due to its high atomic number and density. The contrast agent highlights the blood supply to the anatomy of interest (e.g., legs, heart, or other organs).

In another example, a mask may be generated from a series of post-contrast mask frames 352 as shown in FIG. 3B. The post-contrast mask generation is performed during the roadmap sequence 350 shown in FIG. 3B. In the regional roadmap sequence 350 shown in FIG. 3B, the mask frames 354 are acquired immediately after the contrast agent is injected. In one example, the contrast agent is injected at time t0, at the start of the sequence 350. After a threshold number of mask frames (e.g., 8, 16 or 32 frames) are acquired, at time t1, a road map mask M' (358) may be determined by peak opacification. For example, the mask M' may be generated using equation (1B) as shown below:

$$\text{Mask, } \underline{M'} = \text{Peakopacificity}\{m(k), k=0,1,\ldots,N-1\} \tag{1B}$$

where N is the total number of mask frames acquire between time t0 and t1. Peak Opacification is used to visually enhance vasculature with contrast media. Contrast media flows through a vessel during x-ray acquisition. However, at the end of the exposure, contrast media may no longer be visible in the upstream portion of the vessel (as the contrast media is pushed downstream by blood flow, for example). Peak opacification corrects this shortcoming, allowing complete visualization of the vessel, by maintaining darker pixels in the case of iodine based contrast media (or lighter in the case of $CO_2$ media) across all frames during the exposure. Herein, the road map mask M' may be used for subsequent subtraction as shown below to generate subtracted images that are used for guiding and facilitating endovascular manipulation of catheters and guide wires.

Once the mask is generated (either using equation (1A) or (1B)), a fluoroscopic image sequence 303 including fluoroscopic frames 306 may be acquired at time t3. A first fluoroscopic frame 306 is acquired at time t3. In one example, the first fluoroscopic frame 306 is acquired immediately after the contrast agent is injected (FIG. 3A). In another example, the first fluoroscopic frame 306 is acquired after a threshold number of mask frames are acquired (FIG. 3B). Between time t3 and t(N), N fluoroscopic frames are acquired. For each of the fluoroscopic frames generated at time t3, each of a background frame 310 and an enhanced frame 314 are generated as described below. Herein, the fluoroscopic frames include unsubtracted image data that is generated by the detectors of the imaging system. In some examples, the fluoroscopic frame may be referred as raw data. The background frame and the enhanced frame may be subtracted frames generated from the fluoroscopic frame; however, a level of subtraction applied to the background frame may be different from the level of subtraction applied to the enhanced frame. Thus, the background frame may include more of the anatomical landmarks and less of the vasculature. In contrast, the enhanced frame may include enhanced vasculature, and less of the bony landmarks.

In one embodiment, the background frame may be the same as the fluoroscopic frame 306 as shown by equation (2) below:

$$b(k)=f(k) \tag{2}$$

where $b(k)$ represents $k^{th}$ background frame and $f(k)$ represents the $k^{th}$ fluoroscopic frame. In such an example, the background frame does not include any subtraction. In such an example, the background frame may be interchangeably referred to as the fluoroscopic frame.

In some examples, the background frame $b(k)$ may be centered by applying an offset as shown by equation (3) below:

$$b(k) = f(k) + C_1 \quad (3)$$

where $C_1$ is an integer (positive or negative) offset value that is added to center the background frame.

Additionally, a first amount or percentage of the mask may be subtracted from the fluoroscopic frame f(k) as shown in equation (4) below:

$$b(k) = f(k) - (\alpha_1 * m) + C_1 \quad (4)$$

where $\alpha_1$ is a constant that represents the amount by which the mask m (DSA mask M or roadmap mask M') is subtracted from the fluoroscopic frame f(k). In some examples, a correction, which takes into account motion induced artifacts, is applied to the fluoroscopic frame as discussed below. For example, any movements occurring while acquiring the fluoroscopic sequence 303 may induce motion artifacts in the fluoroscopic frame 306. The corresponding background frame 310 generated from the fluoroscopic frame may include a correction or shifting that adjusts for any motion-induced artifact. As an example, while acquiring the fluoroscopic sequence f(k), if the subject moves, and/or if the table upon which the subject rests is jerked, the region of the anatomy of interest that is being imaged may be displaced in the subsequent frames.

Motion or displacement correction includes shifting the mask. Typically, the mask is modified shifting the pixel at (i,j) to (i+δi,j+δj) to generate a new mask (m̂) as shown by equation (5) below:

$$\hat{m}_{i,j} = m_{i+\delta i, j+\delta j} \quad (5)$$

where $m_{i,j}$ is the element of the mask M (equations (1A) or (1B)) located at (i,j). The new mask $\hat{m}_{i,j}$ is then applied in the subtracting.

In equation (4), $\alpha_1$ may be referred to as a weight. The constant $\alpha_1$ may be selected from a range between 0 and 1. When $\alpha_1=1$, then the background frame b(k) is a purely subtracted frame, meaning that the mask m is entirely subtracted from the fluoroscopic frame 306 to generate the background frame b(k). In such an example, the background frame may include only the vasculature, having had the landmarks of bones and vessels subtracted out. For the DSA technique, the subtracted background frame may include increased contrast and enhanced visibility of the vasculature that is highlighted by the contrast media. For the roadmap technique, the subtracted background frame may include enhanced visualization of the interventional devices. In one example, the value of $\alpha_1$ may be input by a user at the start of the imaging sequence 300 (e.g., at time t0). In another example, the value of $\alpha_1$ may be input by the user at the end of the mask sequence (e.g., time t1). In yet another example, the value of $\alpha_1$ may be dynamically changed during the imaging sequence by the user in real-time. For example, the user may be able to change $\alpha_1$ by adjusting a slider to dynamically adjust the value of $\alpha_1$. In other examples, the value of $\alpha_1$ may be adjusted by the imaging system based on user input preferences. Changing the value of $\alpha_1$ changes the amount of the mask that is subtracted from the fluoroscopic frame. It may be noted that the process of subtraction occurs in real-time, without any significant delay or post-processing steps.

As discussed above, the processes disclosed herein may be performed in real-time. The real-time processing may be realized by dynamically adjusting the amount of the mask to be subtracted from the fluoro image inside and outside the ROI, dynamically changing the size of the ROI, and/or dynamically moving the ROI to follow the movement of, for instance, a tip of a guidewire. All of the above dynamic adjustments/movements of the ROI and subtraction may be performed while imaging, rather than at a later time, although such processing could also occur after imaging is complete (e.g., the processes could be performed on one or more saved images).

In this way, a background sequence 312 may be generated from the fluoroscopic sequence 303. Herein, each background frame 310 of the background sequence 312 may be generated from each individual fluoroscopic frame 306 as described by equation (4). In addition, an enhanced sequence 316 may be generated form the fluoroscopic sequence as shown in equation (6) below:

$$e(k) = f(k) - (\alpha_2 * m) + C_2 \quad (6)$$

where f(k) is the fluoroscopic frame 306, m is the mask generated as shown by equations (1A) or (1B), $\alpha_2$ and $C_2$ are coefficients similar to the coefficients $\alpha_1$ and $C_1$ as described previously with reference to equations (3) and (4). Briefly, $\alpha_2$ is a weight that represents the amount by which the mask m (e.g., M or M') is subtracted from the fluoroscopic frame f(k). In one example, $\alpha_2$ may be different from $\alpha_1$. In an example, $\alpha_2$ may be greater than $\alpha_1$, in which case the amount of subtraction that is applied to the enhanced frame is larger than the background frame. In yet another example, $\alpha_2$ may be smaller than $\alpha_1$, in which case the amount of subtraction that is applied to the enhanced frame is smaller than the background frame. Similar to $\alpha_1$, the coefficient $\alpha_2$ may be selected from a range between 0 and 1. When $\alpha_2=1$, then the background frame b(k) is a purely subtracted frame, meaning that the mask m is entirely subtracted from the fluoroscopic frame 306 to generate the enhanced frame e(k). In such an example, the background frame may include only the vasculature, having had the landmarks of bones and vessels subtracted out.

As described previously with reference to $\alpha_1$, the value of $\alpha_2$ may be input by a user at the start of the imaging sequence 300 (e.g., at time t0). In another example, the value of $\alpha_2$ may be input by the user at the end of the mask sequence (e.g., time t1). In yet another example, the value of $\alpha_2$ may be input after the background frame is generated. In still other examples, the value of $\alpha_2$ may be dynamically changed during the imaging sequence by the user in real-time. Specifically, the user may be able to change $\alpha_2$ by adjusting a slider to dynamically adjust the value of $\alpha_2$ in real-time. Herein, the slider to adjust $\alpha_1$ may be different from the slider to adjust $\alpha_2$, for example. In another example, both $\alpha_1$ and $\alpha_2$ may be adjusted using different slider bars arranged within a single window. In yet another example, the value of $\alpha_2$ may be adjusted based on the value of $\alpha_1$. If the user has set the value of $\alpha_1$ to 0.5, the value of $\alpha_2$ may be automatically adjusted to 0.75 (e.g., 1.5*$\alpha_1$), for example. Changing the value of $\alpha_2$ changes the amount of the mask that is subtracted from the fluoroscopic frame to generate the enhanced frame e(k). It may be noted that the process of subtraction occurs in real-time, without any significant delay or post-processing steps. In this way, the enhanced sequence 316 may be generated from the fluoroscopic sequence 303. Herein, each enhanced frame 314 of the enhanced sequence 316 may be generated from each individual fluoroscopic frame 306 as described by equation (6). In addition, the enhanced frame, which is a subtracted frame, may be displayed to enhance the visibility of the vascular structures in the anatomy of interest.

The subtracted frames are also referred to as DSA images or roadmap images, and the unsubtracted frames may be referred to as landmark images. The DSA images enhance the visibility of the vascular structures of the anatomy by subtracting or removing the bony structure (which is present in the mask) of the anatomy. The roadmap images may include images with enhanced visibility of the interventional device.

Typically, the final DSA/roadmap image that is displayed may be mixed with a certain percentage of the unsubtracted frame to partially bring the bony structure back so as to generate the so-called landmark images. Herein, the percentage of unsubtracted frame added is applied to the entire frame (e.g., entire area of the frame), and hence degrades the visibility of vasculature of the final image displayed on the display making it harder for the user to diagnose vascular anomalies or perform interventional procedures. Specifically, in DSA imaging, when the landmark images having bony structures are included in the DSA frame, the visibility of the vasculature may be degraded compared to the pure DSA image. Likewise, in roadmapping, when some of the unsubtracted frame is added back, the visibility of the interventional devices may be reduced. Generally, the landmark images are displayed on one channel and/or display, and the subtracted image (e.g., background/enhanced frame of the DSA/roadmap image) may be displayed on a different channel and/or display. The user may have to look at the subtracted image, and additionally look at the unsubtracted landmark images displayed on a different monitor to understand the position of the vasculature relative to the landmarks. However, the inventors have recognized that it is possible perform regional DSA and regional roadmap including landmarks as described below. Briefly, the mask generated using equations (1A) or (1B) may be weighted differentially within the fluoroscopic frame. As a result, the final image may include regions that have larger amount of subtraction, and regions that have smaller amounts of subtraction all within the same image. Thus, the final image that is displayed may include both anatomical landmarks and vasculature.

In one embodiment, the enhanced frame may be generated within a region-of-interest (ROI) 318 selected by the user, and may displayed within the background frame 310 as shown in the regional DSA sequence 326 (FIG. 3A) and roadmap sequence 360 (FIG. 3B). In both imaging methods, the ROI 318 may be selected by a user by selecting a shape from a set of pre-defined shapes as shown in FIG. 4, or may include a user-defined shape specific to the anatomy being imaged as shown in FIG. 5.

Turning to FIG. 4, view 400 shows some example ROI shapes. Some non-limiting example shapes of the ROI include a circle 408, a squircle 410, and a square 412. In one example, the user may select the shape of the background image and the ROI at the start of the imaging sequence. In another example, the user may select the shape of both the background image and the ROI based on the images displayed on a display (e.g., monitor). The user may additionally select a shape of the background image. Some non-limiting example shapes of the background frame include a square 402, a squircle 404, and a circle 406. These example shapes of the ROI and the background frame may be combined in several ways; some non-limiting combinations are shown in view 400. In some examples, more than one ROI may be selected by the user. In such examples, the amount of subtraction within each of the ROI may be specified by the user. As previously described, the background frame outside the ROI may include less subtraction and hence more of the landmark features, and the region inside the ROI may include more subtraction, and hence less of the landmark features.

In one example, the user may be able to draw a user-defined shape specific to the anatomy that is imaged as shown in FIG. 5. FIG. 5 shows an example 500 of a background image 508 displaying an anatomy. Specifically, the background image 508 includes a square shape 502. However, as described with reference to FIG. 4, the background image may include other shapes such as circle, squircle, and the like. Herein, the background image may be displayed by subtracting a first level (given by $\alpha 1$) of the mask M from a corresponding fluoroscopic image as described by equation (4). In one specific example, when $\alpha_1$ is set to zero, the background image may be a purely unsubtracted image having more bone and vessel information. In other examples, the value of $\alpha 1$ may be selected from a range of values as described with reference to FIG. 3A.

Additionally, the user 506 may be able to draw a shape 504 inside the background image 508 to specify a ROI 510. As such, the user may use a mouse to drag a cursor and trace the ROI 510 on the display showing the background image 508. In another example, the user may touch the display and use his/her finger(s) to draw the shape 504 directly on the background image 508. In yet another example, the user may select the ROI 504 from a set of user-defined shapes.

Once the user draws the shape of the ROI, the imaging processor may automatically apply a second level of subtraction (given by $\alpha_2$, as defined in equation (6)) to the region inside the ROI. In addition, the region outside the ROI may be maintained at the first level of subtraction. In one example, when $\alpha_2 > \alpha_1$, the region inside the ROI may include more subtraction and hence higher contrast for viewing the vasculature relative to the landmark images displayed on the region outside the ROI (having lesser subtraction). In other examples, $\alpha_2$ may be lower than $\alpha_1$, in which case the region inside the ROI may include the landmarks, and the region outside the ROI may include the vasculature. The user may be able to dynamically adjust the values of the $\alpha_2$ and $\alpha_1$ to change the levels of subtraction applied to each of the region inside the ROI and outside the ROI. In addition, the user may be able to adjust one or more of the size, shape, and location of the ROI as described in FIGS. 6A-D in real-time.

Turning now to FIGS. 6A-D, example maneuvers performed by the user to dynamically position the ROI are shown. Specifically, the user may be able to dynamically adjust a size of each of the subtracted image and the unsubtracted image displayed within and outside the ROI respectively. In FIGS. 6A-D, the image on the left shows that type of maneuver or action that is performed on the ROI, and resulting ROI is shown on the right.

Figure 6A:
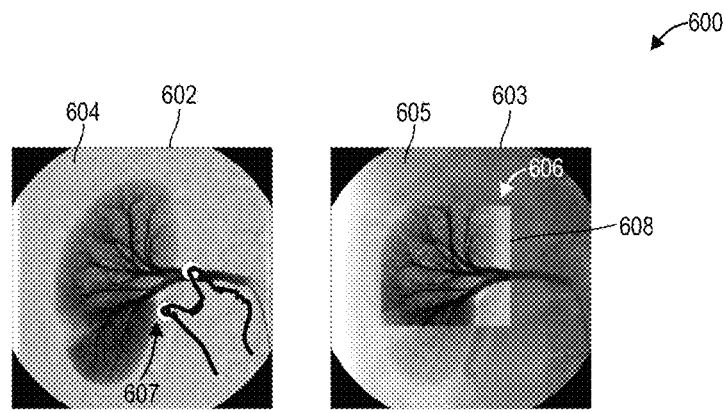
FIGS. 6A-D show example operations performed by the user to adjust one or more of a size, a shape, and a position of the ROI inside the fluoroscopic image according to an embodiment of the invention.
Figure 7:
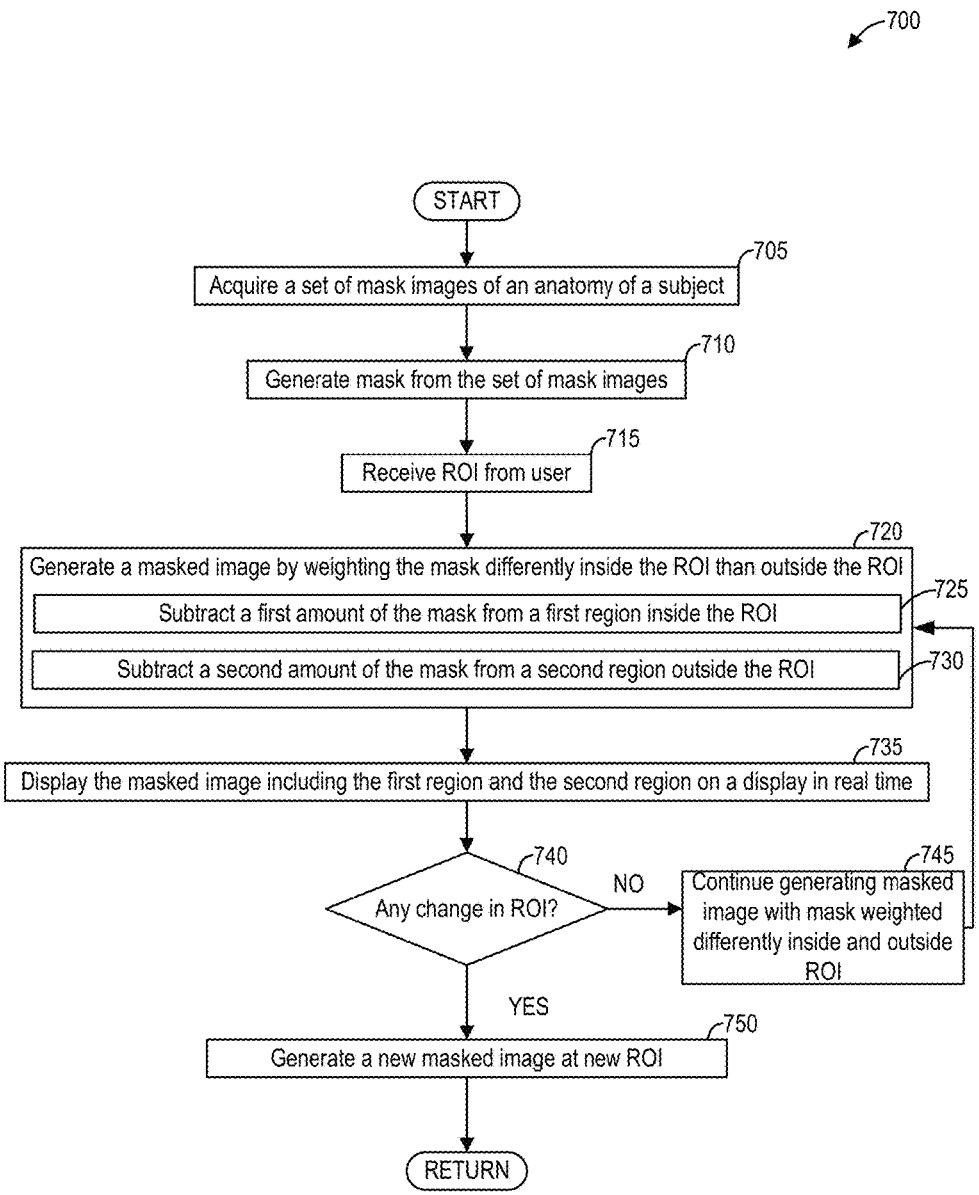
FIG. 7 is a high-level flow chart illustrating an example method for generating a masked image by applying the mask to acquired image data of an anatomy of a subject according to an embodiment of the invention.

In FIG. 6A, a first fluoroscopic image 602 generated from fluoroscopic x-ray image data of an anatomy is shown. Using equation (4), a first background image 604 of the first fluoroscopic image 602 may be generated. In one example, a first level of subtraction (given by $\alpha_1$, for example) may be applied to the fluoroscopic image data to generate the background image 604 (also referred to as a masked image). Specifically, a mask m (e.g., DSA mask M or roadmap mask M') may be generated prior to acquiring the fluoroscopic image data. The first background image may be generated by subtracting the first amount of the mask m from the fluoroscopic image data, and additionally applying displacement correction.

In one example, the value of $\alpha_1$ may be set to 1, indicating that the resulting background image is a fully subtracted image. In another example, the value of $\alpha_1$ may be set to 0, meaning that the background image does not include any subtraction, and hence includes landmarks such as bones, vessels, and the like. In other examples, the level of subtraction may be dynamically varied as discussed earlier with reference to FIGS. 3A-B. In addition to the subtraction level, the user may specify a shape (e.g., circular) of the background image.

The user may be able to select the size, shape, a number, and location of the ROI using several methods. One non-limiting example method includes performing touch operations on a touchscreen of a display on which the background image is displayed. In one example, the user may be able to select the ROI by performing a touch operation 607 inside the first background image 604. One example touch operation 607 may include the user touching inside the background image with one or more fingers. Performing the touch operation 607 may automatically activate a ROI selection menu. From the menu of preselected shapes (e.g., circle, square, circle, and the like), or from a user defined shape, the user may be able to select a particular shape (e.g., square) of the ROI 608 as shown in the image on the right in FIG. 6A.

After selection of the ROI, a second fluoroscopic image 603 is shown. The second fluoroscopic image 603 includes a second background image 605. The second background image 605 may be generated by subtracting a first level L1 of the mask m from the fluoroscopic image data in the regions outside the ROI 608. In addition, a first enhanced image 606 is generated inside the ROI 608. A second level L2 of the mask m may be subtracted from the fluoroscopic image data inside the ROI 608 to generate the enhanced image 606 inside the ROI 608. Thus, the enhanced image 606 including vasculature is displayed only inside the ROI 608, while the outside of the ROI includes landmarks. Herein, the subtraction applied to each of the second background image 605 and the first enhanced image 606 includes a pixel-to-pixel subtraction of the mask m, with different weights applied to the pixel values inside and outside the ROI 608. In this way, both the second background image 605 and the first enhanced image 606 may be displayed together on the same display, in the same frame, so that user may be able to visualize the enhanced vasculature (or interventional devices) inside the enhanced image (e.g., inside ROI 608) relative to the landmarks displayed on the outside (e.g., background image 605). If placing a stent or a wire, the user may be able to traverse the vasculature with the aid of the landmarks displayed around the enhanced image 606. Furthermore, the user may be able to adjust a size, shape, and location of the enhanced image (or ROI) as described below.

Figure 6B:
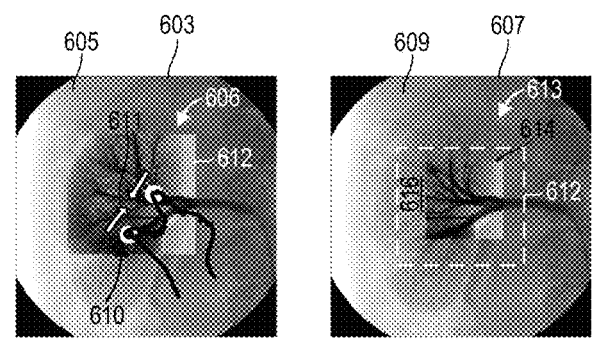

The size of the ROI 608 may be adjusted by performing a touch operation 610 within the ROI 608 of the second fluoroscopic image 603 as shown in FIG. 6B. By moving the fingers inwards (as indicated by arrows 611), the user may perform a "pinch" operation to reduce the size of the ROI. A third fluoroscopic image 607 is shown on the right side in FIG. 6B. The resulting ROI 614 includes a smaller area when compared to the original ROI 618. The amount by which the ROI 614 is reduced in size may be based on an amount of "pinching" performed within the ROI 612. Herein, the amount of pinching may be determined based on or more of a pressure applied to the display (sensed by pressure sensors included in the display), distance through which the fingers are moved inside the ROI 612, a rate at which the fingers are moved, and the like. In one example, once the desired size is reached, the user may remove his/her fingers from the display indicating that the desired size is reached. In another example, the user may tap the display twice to stop at the desired size of the ROI 614. When transitioning from ROI 612 to ROI 614, the size of the ROI is reduced, hence a second enhanced image 613 is now generated over a smaller region (within ROI 614) and displayed inside a third background image 609.

When ROI 614 is specified, a third background image 609 is generated outside ROI 614, and a second enhanced image 613 is generated inside the ROI 614. As before, the second enhanced image may include a third level L3 of mask m subtracted from the fluoroscopic image data, and the third background image may include a fourth level L4 of the mask m subtracted from the fluoroscopic image data. The first, second, third, and the fourth levels of subtraction may be dynamically adjusted by the user.

In one example, L3 may be equal to L2 and L4 may be equal to L1. In such an example, a difference given by (L2−L1) may be added to the second background image 605 to generate the third background image 609 in the region 616 between the ROI 612 and ROI 614.

In one example, the second enhanced image 613 displayed within ROI 614 may be a purely subtracted image (e.g., where $\alpha_2=1$), and the background image may be a purely unsubtracted image (e.g., where $\alpha_1=0$). In another example, the user may be able to adjust values of $\alpha 1$ and $\alpha 2$, to change the amount of subtraction applied inside the outside the ROI 614.

Figure 6C:
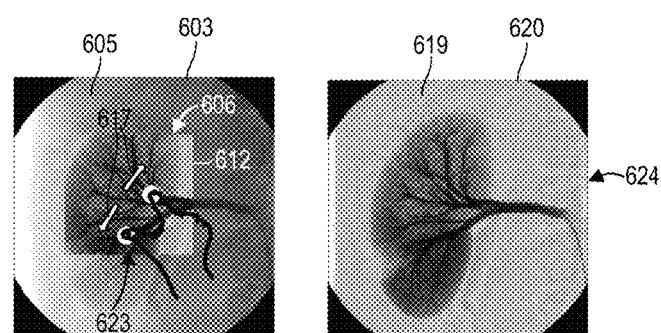

In another example, the user may be able to increase the size of the ROI 612 as shown in FIG. 6C. The user may be able to perform an operation 623 inside the ROI 612 to increase the size of the ROI. The user may move the fingers outwards (as indicated by arrows 617), the user may perform an "expand" operation to increase the size of the ROI 612. Herein, the amount of expansion may be determined based on or more of a pressure applied to the display (sensed by pressure sensors included in the display), distance through which the fingers are moved inside the ROI 612, a rate at which the fingers are moved, and the like. In one example, once the desired size is reached, the user may remove his/her fingers from the display indicating that the desired size is reached. In another example, the user may tap the display twice to stop at the desired size. In one example, the ROI 612 may be expanded to a maximum size, as shown in the right side image of FIG. 6C. For example, the ROI 612 may be expanded to an ROI 624, which covers the entire area of the fluoroscopic image 620. The resulting background image 619 may include a fully subtracted image (similar to the first background image 604 shown in FIG. 6A). In this way, the user may be able to adjust the size of the ROI and hence the area in which the subtraction is performed within the background image.

In general, when a size of the ROI is increased or decreased, the size of the background image outside the ROI is decreased or increased, respectively. Thus, displaying the image with the adjusted ROI may include recalculating one or more of the background image b(k) and the enhanced image e(k) based on equations (4) and (5) using the new ROI size and position. For example, when the ROI is decreased, e(k) may be calculated over the new decreased ROI, and additionally b(k) may be calculated over a new increased region. Likewise, when the ROI is increased, e(k) may be calculated over the new increased ROI, and additionally b(k) may be calculated over a new decreased region. In this way, both the enhanced image and the background image may be constantly updated based in user selection.

Figure 6D:
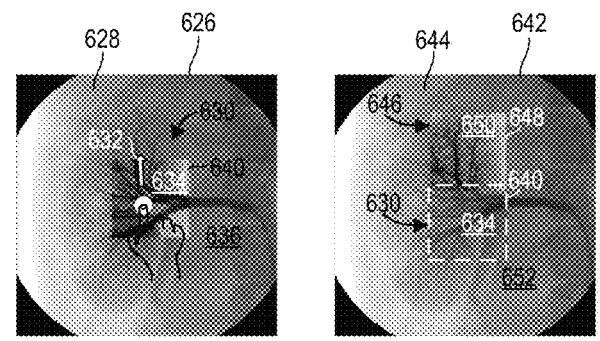

In one example, the user may be able to move the ROI from a first location 630 to a second location 646 in real-time t0 follow the flow of the contrast media or progress of the guidewire as shown in FIG. 6D. As described previously, a background image 628 may be generated from a fluoroscopic image 626 by applying a mask subtraction to the fluoroscopic image 626. An ROI 640 may be selected inside the background image 628 (as described previously with reference to FIG. 6A). Initially, a boundary of the ROI 640 (herein a square boundary) may be selected and positioned at the first location 630 within the fluoroscopic image 626. Based on the location and size of the ROI, a first amount of subtraction may be applied to the region inside the ROI 640 to generate an enhanced image inside the region 634 and a second, different amount of subtraction may be applied to the region 636 outside the ROI 640 to generate the background image in the region 636. In some examples, the region inside the ROI may be referred to as a first region 634, and the region outside the ROI may be referred to as a second region 636. The first region 634 may include an enhanced image generated using equation (7), given below $$e = f - A1 + C \quad (7)$$

where e represents a representative pixel value in the first region 634, f is a representative pixel value of the fluoroscopic image 626, and C is an offset applied to the pixel value e. Herein, A1 may be equal to ($\alpha_2$*m), for example, where m is the pixel value of the mask applied with a weight $\alpha_2$, as described previously.

Likewise, the second region 636 may include a background image generated using equation (8), given below $$b = f - A2 + C \quad (8)$$

where b is a representative pixel value in the second region 636, and f is a representative pixel value of the fluoroscopic image 626, and C is the offset. Herein, A2 may be equal to ($\alpha_1$*m), for example, where m is the pixel value of the mask applied with a weight $\alpha_1$, as described previously.

As such, the first amount of the subtraction is performed only inside the boundary of first region, and the enhanced image is generated only within the boundary of the first region. Additionally, both the first region and the second region may be displayed on the same display. The user may touch the display inside the boundary of the first region 634 and drag the first region 634 from the first location 630 to a new, second location 646 inside the fluoroscopic image 626 along a direction indicated by arrow 632. At the new location 646, a new fluoroscopic image 642 including a new background image 644 is generated. Based on the location and size of the ROI, a first amount of subtraction may be applied to the region inside the ROI 648 (region 650) and a second, different amount of subtraction may be applied to the region outside the ROI 648 (region 652). The image processor may adjust an amount of subtraction of the fluoroscopic image applied to the regions inside and outside the ROI 648 as described below. The subtracting weight applied inside the ROI versus outside the ROI may remain constant even as the ROI is moved from the first location 630 to the second location 646. In one example, the ROI 640 may include 100% subtraction (e.g., $\alpha_2 = 1$, or 100% of the mask is entirely subtracted from the fluoroscopic image) and the region outside the may ROI include 0% subtraction ($\alpha_1 = 0$). This is shown in the figure on the left in FIG. 6D. When the ROI is moved to the second location (as shown figure on the right in FIG. 6D), the amount of subtraction performed inside the ROI 648 will still be 100%, whereas the amount of subtraction performed in region outside the ROI (given by 652) will be 0%. Thus, $\alpha_2$ will be set to 1 at ROI 648 and $\alpha_1$ will be set to 0 in ROI 640. The amount of mask that is subtracted within the ROI at the new location and the amount of mask that is added to the ROI located at the previous location may be calculated as shown below.

For example, a third amount of the mask may be subtracted from the background image in the first region 650 inside the ROI 648 at the second location 646, the third amount being equal to a difference between the first amount and the second amount. Mathematically, the first region 650 may be represented as shown below $$e' = b - A3 \quad (9)$$

where e' is a representative pixel value in the first region 650 at the second location 646, and b is given by equation (7). Likewise, the second region 652 may be generated using equation (10), given below $$b' = e + A3 \quad (10)$$

where b' represents pixel values in the second region 652 at the second location 646, and e is given by equation (7). As such, the third amount may be equal to a difference between the first amount and the second amount (e.g., A2−A1).

In some examples, more than one ROI may be specified by the user. In such an example, the mask may be weighted different across different regions of interest based on user input. The user may additionally be able to move the different regions of interest independent of one another.

Further, the image data used to generate the various images illustrated in FIGS. 6A-6D may be the same raw image data, e.g., the image data used to generate the first fluoroscopic image 602 may be the same image data used to generate the second fluoroscopic image 603. In other examples, different image data may be used to generate the various images illustrated in FIGS. 6A-6D, e.g., a first set of image data collected at a first time may be used to generate the first fluoroscopic image 602 while a second set of image data collected at a second, later time may be used to generate the second fluoroscopic image 603.

Thus, a first example method may be carried out by the components and systems depicted in FIGS. 1-2 (such as image processing unit 110 of FIG. 1, and/or image processor 230 of FIG. 2); however, it should be understood that the method may be implemented on other components and systems not depicted without departing from the scope of the present disclosure. The first example method may include generating a mask of an anatomy of a subject; subtracting a first amount of the mask from a fluoroscopic image of the anatomy of the subject, the first amount of the mask subtracted only inside a boundary of a first region of the fluoroscopic image, subtracting a second amount of the mask from the fluoroscopic image from a second region outside the boundary of the first region, and displaying the fluoroscopic image having both the first region and the second region on a display. Additionally or alternatively, the boundary of the first region may be defined by a user. Additionally or alternatively, the method may further include responsive to the user touching the display inside the boundary of the first region on the monitor and dragging the first region from a first location to a new, second location inside the fluoroscopic image, subtracting a third amount of the mask from the fluoroscopic image inside the boundary of the first region at the second location, the third amount equal to a difference between the first amount and the second amount. Additionally or alternatively, the method may include adding the third amount of the mask inside the boundary of the first region of the fluoroscopic image at the first location. Additionally or alternatively, the method may include responsive to the user touching the monitor inside the first region at two points and moving the two points outwardly to increase a distance between the two points, increasing a first area of the first region and decreasing a second area of the second region of the fluoroscopic image, the amount of increase of the first area proportional to the increase in distance between the two points. Responsive to the user touching the monitor inside the first region at two points and moving the two points inwardly to decrease the distance between the two points, the method may additionally or alternatively include decreasing the first area of the first region and decreasing the second area of the second region of the fluoroscopic image, the amount of decrease of the first area proportional to the decrease in distance between the two points.

Turning now to FIG. 7, an example method for generating a masked image by applying a mask to acquired image data of an anatomy of a subject is shown. Specifically, applying the mask includes weighting the mask differently inside a region of interest (ROI) of the image than outside the ROI, the weighting inside ROI being independent of the weighting outside the ROI. Instructions for carrying out method 700 and other example methods described herein may be executed by a controller or processor (e.g., image processing unit 110 of FIG. 1, and/or image processor 230 of FIG. 2) based on instructions stored on a memory of the processor and in conjunction with signals received from sensors of the imaging system, such as the sensors described above with reference to FIGS. 1-2. The controller may employ actuators of the imaging system to adjust the operation of the imaging system, according to the methods described. As an example, during a regional DSA/roadmap sequence, the processor may adjust an output of an x-ray source (such as source 102 shown in FIG. 1 and/or source 205 shown in FIG. 2) to generate image data using a detector (such as detector 108 of FIG. 1, and/or detector 209 of FIG. 2). As another example, the processor may determine a level of pressure applied by the user on a display (e.g., monitor) based on an output generated by one or more pressure sensors coupled to the display.

Method 700 begins at 705 where a set of mask images are acquired. In one example, the mask images may be pre-contrast images acquired prior to injection of a contrast agent into the anatomy of the subject. In another example, the mask images may be post-contrast images acquired for immediately after the injection of the contrast agent. As such, a number of mask images acquired may be adjusted based on noise levels of the system, specification of the detector used, user preference, and the like.

At 710, method 700 includes generating a mask from the mask images acquired at 705. In one example, the mask may be generated by averaging a set of pre-contrast mask images using equation (1A). In another example, the mask may be generated by measuring the peak opacity of a set of post-contrast mask images using equation (1B).

At 715, method 700 includes receiving a region of interest (ROI) of the image data from a user. The image data may include one or more of raw fluoroscopic image, background image or other suitable image data. In one example, the ROI selection may be enabled through multi-touch of a monitor displaying the fluoroscopic image of the anatomy. Additionally, the user may select a shape, a size, and a location of the ROI as described previously with reference to FIGS. 4, 5, and 6A-D. The ROI may define a boundary that delineates a first region from a second region, wherein the first region refers to the region inside the ROI, and the second region includes the region lying outside the ROI (however, inside the fluoroscopic/background image). In some examples, more than one ROI may be received from the user.

At 720, method 700 includes generating a masked image by weighting the mask (generated at 710) differently inside the ROI than outside the ROI. Weighting the mask includes subtracting a first amount of the mask from the first region inside the ROI at 725, and further includes subtracting a second amount of the mask from the second region outside the ROI at 730. While differential subtraction is provided as one example method for which the ROI may be weighted differently than outside the ROI, other methods are possible. For example, the mask and image data may be averaged, where the ROI is averaged according to a first weighted average and outside the ROI is averaged according to a second, different weighted average As such, each of the first amount and the second amount may be adjusted dynamically by the user. In one example, the first amount may be set to 0.9, and the second amount may be set to 1. In this example, the first region may include some bony structure that may be used as a landmark for the purely subtracted image displayed inside the second region. At 735, the masked image including both the first region and the second region may be displayed (e.g., on a monitor). If the user specifies more than one ROI, then the mask is weighted differently within each of the ROI based on user preference. For example, if the user defines two ROI, the user may additionally specify the level of subtraction applied to each of the ROI. Additionally, the user may specify the level of subtraction that is applied to the region outside the two ROI.

At 740, method 700 includes checking for any changes in the ROI, changes including, but are not limited to, changes in size, shape, number, and location of the ROI. As described earlier with reference to FIGS. 6A-D, the user may be able to dynamically increase or decrease the ROI size by performing operations including moving fingers inside the masked image. In one example, moving the fingers outwardly may increase the size of the ROI, and moving the fingers inwardly may decrease the size of the ROI. Additionally or alternatively, method 700 may include checking if there are any changes to the first and second amounts of subtraction.

If there is no change in the ROI (e.g., "NO" at 740), then method proceeds to 745, where the masked image may be continued to be generated in the successive frames by subtracting the first amount of the mask from the first region and the subtracting the second amount from the second region.

However, if there is a change in the ROI (e.g., "YES' at 740), then method 700 proceeds to 750, where a new masked image is generated. In some examples, generating a new masked image includes generating the masked image for a new ROI size and/or shape at the same location. Additionally or alternatively, generating a new masked image includes performing the subtractions at a new ROI location specified by the user. Additionally or alternatively, generating the new masked image includes applying different levels of subtraction to the first region and/or the second region based in user input. Method 700 returns.

The technical effect of applying varying levels of subtraction inside and outside the ROI is that the masked image generated in this way includes a regionally subtracted image within an image having variable landmarks. In this way, landmark structures and detailed vasculature information may be included in the same image making it easier for diagnostic purposes. In addition, this may increase the accuracy of placement of interventional devices.

The systems and methods described above provide for a method, the method, comprising generating a mask from a set of mask images of an anatomy of a subject, and generating a masked image by applying the mask to acquired image data of the anatomy of the subject, including weighting the mask differently inside a region of interest (ROI) of the image data than outside the ROI, the weighting inside ROI independent of the weighting outside the ROI. In a first example of the method, the method may additionally or alternatively include wherein the weighting includes subtracting a first amount of the mask from a first region inside the ROI and subtracting a second amount of the mask from a second region outside the ROI, the masked image including the first region and the second region. A second example of the method optionally includes the first example, and further includes wherein the first amount and the second amount are each adjusted based on user preference. A third example of the method optionally includes one or more of the first and the second examples, and further includes wherein the second amount is smaller than the first amount. A fourth example of the method optionally includes one or more of the first through the third examples, and further includes displaying the masked image in real-time on a display. A fifth example of the method optionally includes one or more of the first through the fourth examples, and further includes wherein the ROI is selected by a user, and wherein one or more of a shape, a size, and a position of the ROI within the masked image is adjustable by the user. A sixth example of the method optionally includes one or more of the first through the fifth examples, and further includes wherein the size of the ROI is smaller than a size of the masked image. A seventh example of the method optionally includes one or more of the first through the third examples, and further includes wherein the shape of the ROI includes one or more of a circle, a squircle, a square, an ellipse, and a user-defined shape. An eighth example of the method optionally includes one or more of the first through the third examples, and further includes wherein the mask is generated by averaging the set of mask images acquired prior to injection of a contrast agent into the anatomy of the subject, and wherein the image data is acquired after the injection of the contrast agent. A ninth example of the method optionally includes one or more of the first through the eighth examples, and further includes wherein the mask is generated by performing a peak opacification operation on the set of mask images acquired immediately after an injection of a contrast agent, and wherein the image data is acquired after the mask is generated.

The systems and methods described above provide for a method, the method, comprising generating a mask of an anatomy of a subject; subtracting a first amount of the mask from a fluoroscopic image of the anatomy of the subject, the first amount of the mask subtracted only inside a boundary of a first region of the fluoroscopic image, subtracting a second amount of the mask from the fluoroscopic image from a second region outside the boundary of the first region, and displaying the fluoroscopic image having both the first region and the second region on a display. In a first example of the method, the method may additionally or alternatively include wherein the boundary of the first region is defined by a user, and further comprising responsive to the user touching the display inside the boundary of the first region and dragging the first region from a first location to a new, second location inside the fluoroscopic image, subtracting a third amount of the mask from the fluoroscopic image inside the boundary of the first region at the second location, the third amount equal to a difference between the first amount and the second amount. A second example of the method optionally includes the first example, and further includes adding the third amount of the mask inside the boundary of the first region of the fluoroscopic image at the first location. A third example of the method optionally includes one or more of the first and the second examples, and further includes responsive to the user touching the monitor inside the first region at two points and moving the two points outwardly to increase a distance between the two points, increasing a first area of the first region and decreasing a second area of the second region of the fluoroscopic image, the amount of increase of the first area proportional to the increase in distance between the two points. A fourth example of the method optionally includes one or more of the first through the third examples, and further includes responsive to the user touching the monitor inside the first region at two points and moving the two points inwardly to decrease the distance between the two points, decrease the first area of the first region and decrease the second area of the second region of the fluoroscopic image, the amount of decrease of the first area proportional to the decrease in distance between the two points.

The systems and methods described above also provide for an imaging system, the system, comprising an x-ray source configured to excite an anatomy of a patient, an imaging device configured to generate a fluoroscopic image sequence of the anatomy in real-time in response to x-ray radiation detected by a detector, a display with a user interface configured to display the fluoroscopic image sequence, a controller operably coupled to the display and the imaging device and configured with instructions in non-transitory memory that when executed cause the controller to: generate a mask by averaging a series of frames at a start of the fluoroscopic image sequence, generate a background image sequence of the anatomy after generating the mask, receive an indication of a region of interest (ROI) from the user via the user interface, dynamically subtract a first amount of the mask from each image of the background image sequence only inside the ROI to generate a subtracted sequence, and display a regional digital subtracted angiography (DSA) image sequence having the subtracted image sequence inside the ROI and the background image sequence outside the ROI. In a first example of the system, the system may additionally or alternatively include wherein averaging the series of frames includes averaging a series of frames prior to injection of a contrast agent into the patient. A second example of the system optionally includes one or more of the first and the second example, and further includes wherein averaging the series of frames includes performing a peak opacification operation on a series of frames acquired immediately after injecting a contrast agent into the patient. A third example of the system optionally includes one or more of the first and the second examples, and further includes wherein the first amount is adjusted by the user. A fourth example of the system optionally includes one or more of the first through the third examples, and further includes wherein the ROI is selected by the user and includes one or more a circle, a squircle, a square, an ellipse, and a user-defined shape.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising," "including," or "having" an element or a plurality of elements having a particular property may include additional such elements not having that property. The terms "including" and "in which" are used as the plain-language equivalents of the respective terms "comprising" and "wherein." Moreover, the terms "first," "second," and "third," etc. are used merely as labels, and are not intended to impose numerical requirements or a particular positional order on their objects.

This written description uses examples to disclose the invention, including the best mode, and also to enable a person of ordinary skill in the relevant art to practice the invention, including making and using any devices or systems and performing any incorporated methods. The patentable scope of the invention is defined by the claims, and may include other examples that occur to those of ordinary skill in the art. Such other examples are intended to be within the scope of the claims if they have structural elements that do not differ from the literal language of the claims, or if they include equivalent structural elements with insubstantial differences from the literal languages of the claims.

The invention claimed is:

1. A method, comprising:
    generating a mask from a set of mask images of an anatomy of a subject;
    applying the mask to acquired image data of the anatomy of the subject to generate a masked image, wherein applying the mask includes weighting the mask differently inside a first user-defined region of interest (ROI) of the image data than outside the first user-defined ROI, the weighting inside the first user-defined ROI determined independently of the weighting outside the first user-defined ROI; and
    responsive to a user input defining a second user-defined ROI, applying the mask to the masked image, wherein applying the mask to the masked image includes weighting the mask differently inside the second user-defined ROI than outside the second user-defined ROI.

2. The method of claim 1, wherein the weighting includes subtracting a first amount of the mask from a first region inside the first user-defined ROI and subtracting a second amount of the mask from a second region outside the first user-defined ROI, the masked image including the first region and the second region.

3. The method of claim 2, wherein the first amount and the second amount are each adjusted based on user preference.

4. The method of claim 2, wherein the second amount is smaller than the first amount.

5. The method of claim 1, further comprising displaying the masked image in real-time on a display, and wherein the weighting of the mask differently inside the first user-defined ROI than outside the first user-defined ROI includes not subtracting the mask from the acquired image data outside the first user-defined ROI.

6. The method of claim 5, wherein one or more of a shape, a size, and a position of the first user-defined ROI within the masked image is adjustable by the user.

7. The method of claim 6, wherein the size of the first user-defined ROI is smaller than a size of the masked image.

8. The method of claim 6, wherein the shape of the first user-defined ROI includes one or more of a circle, a squircle, a square, an ellipse, and a user-defined shape.

9. The method of claim 1, wherein the mask is generated by averaging the set of mask images acquired prior to injection of a contrast agent into the anatomy of the subject, and wherein the image data is acquired after the injection of the contrast agent.

10. The method of claim 1, wherein the mask is generated by performing a peak opacification operation on the set of mask images acquired immediately after an injection of a contrast agent, and wherein the image data is acquired after the mask is generated.

11. A method, comprising:
    generating a mask of an anatomy of a subject;
    subtracting a first amount of the mask from a fluoroscopic image of the anatomy of the subject, the first amount of the mask subtracted only inside a boundary of a first region of the fluoroscopic image, the boundary of the first region defined by a user by touching a display;
    subtracting a second amount of the mask from the fluoroscopic image from a second region outside the boundary of the first region;
    displaying the fluoroscopic image having both the first region and the second region on the display; and
    responsive to the user touching the display inside the boundary of the first region and dragging on the display the first region from a first location to a new, second location inside the displayed fluoroscopic image, subtracting a third amount of the mask from the displayed fluoroscopic image inside the boundary of the first region at the new second location, the third amount equal to a difference between the first amount and the second amount.

12. The method of claim 11, further comprising adding the third amount of the mask inside the boundary of the first region of the displayed fluoroscopic image at the first location.

13. The method of claim 11, further comprising, responsive to the user touching the display inside the first region at two points and moving the two points outwardly to increase a distance between the two points, increasing a first area of the first region and decreasing a second area of the second region of the displayed fluoroscopic image, the amount of increase of the first area proportional to the increase in distance between the two points.

14. The method of claim 13, further comprising, responsive to the user touching the display inside the first region at two points and moving the two points inwardly to decrease the distance between the two points, decrease the first area of the first region and decrease the second area of the second region of the displayed fluoroscopic image, an amount of decrease of the first area proportional to the decrease in distance between the two points.

15. An imaging system, comprising:
    an x-ray source configured to excite an anatomy of a patient;
    an imaging device configured to generate a fluoroscopic image sequence of the anatomy in real-time in response to x-ray radiation detected by a detector;
    a display with a user interface configured to display the fluoroscopic image sequence;
    a controller operably coupled to the display and the imaging device and configured with instructions in non-transitory memory that when executed cause the controller to:
        generate a mask by averaging a series of frames at a start of the fluoroscopic image sequence;
        generate a background image sequence of the anatomy after generating the mask;
        receive an indication of a region of interest (ROI) from a user via the user interface;
        dynamically subtract a first amount of the mask from each image of the background image sequence only inside the ROI and not subtract the mask from each image of the background image sequence outside the ROI to generate a subtracted sequence; and display a regional digital subtracted angiography (DSA) image sequence having the subtracted sequence inside the ROI and the background image sequence outside the ROI.

16. The system of claim 15, wherein averaging the series of frames includes averaging a series of frames prior to injection of a contrast agent into the patient.

17. The system of claim 15, wherein averaging the series of frames includes performing a peak opacification operation on a series of frames acquired immediately after injecting a contrast agent into the patient.

18. The system of claim 15, wherein the first amount is adjusted by the user.

19. The system of claim 15, wherein the ROI is selected by the user and includes one or more a circle, a squircle, a square, an ellipse, and a user-defined shape.

* * * * *